United States Patent [19]

Funatsu et al.

[11] Patent Number: 5,256,693
[45] Date of Patent: Oct. 26, 1993

[54] GERMICIDAL COMPOSITION

[75] Inventors: Ryoji Funatsu, Tokyo; Kazuyuki Nishizawa, Matsudo; Susumu Mitsui, Koshigaya, all of Japan

[73] Assignee: Somar Corporation, Japan

[21] Appl. No.: 867,367

[22] Filed: Apr. 13, 1992

[30] Foreign Application Priority Data

Jul. 26, 1991 [JP] Japan ............... 3-210156

[51] Int. Cl.$^5$ .............. A01N 33/24; A01N 37/02
[52] U.S. Cl. .................... 514/547; 514/640
[58] Field of Search .................. 514/547, 640

[56] References Cited

U.S. PATENT DOCUMENTS 5,026,723  6/1991  Katayama et al. .......... 514/547

FOREIGN PATENT DOCUMENTS 036055  9/1981  European Pat. Off. .
338440 10/1989  European Pat. Off. .

OTHER PUBLICATIONS

Week 8822, Derwent Publications AN88-150969 Abstract of Japanese Patent JP-A-63 091 303 22 Apr. 1988.
Mitsui et al, C.A. vol. 108 (1988) 108:200220g.

Primary Examiner—Allen J. Robinson
Attorney, Agent, or Firm—Lorusso & Loud

[57] ABSTRACT

A synergistic germicidal composition includes a derivative of α-chlorobenzaldoxime acetate of the general formula (I):

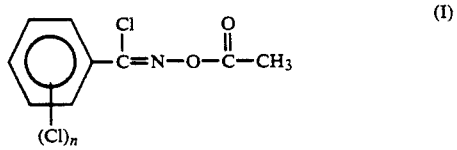

wherein n is an integer of 0 to 2, and 2-bromo-2-nitro-1,3-diacetyloxypropane of the formula (II):

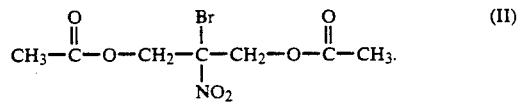

3 Claims, No Drawings

GERMICIDAL COMPOSITION

BACKGROUND OF THE INVENTION

This invention relates generally to a germicide and, more specifically, to a germicidal composition suitable for preventing growth of various germs such as yeasts and filamentous fungi in industrial water such as waste water from pulp mills or cooling water for heat exchangers.

In industrial water such as waste water from paper making steps in pulp-related industries and recirculating cooling water used in various mills, microorganisms such as germs, fungi and bacteria are apt to grow and to cause various problems.

For example, filamentous fungi and yeasts are apt to grow in industrial water used in paper or pulp mills and to form slime within water passages such as pipe walls having roughened surfaces and other portions such as chests and flow boxes through which the water is passed at a low flow rate. The accumulated slimes occasionally depart from their depositing surfaces to cause contamination of paper and pulp products. Other industrial products such as aqueous coating materials, polymer latex, bonding agents, metal machining oils, hides and skins also encounter similar problems. Further, accumulation of slimes also cause blockage of water passages and reduction of heat transfer efficiency.

To cope with these problems, there have been hitherto used organometallic compounds, chlorinated organic compounds, sulfur-containing organic compounds and quarternary ammonium compounds for the prevention of growth of germs in industrial water. These known germicides, however, have certain problems. That is, the known organometallic compounds and chlorinated organic compounds must be used in a large amount in order to obtain satisfactory germicidal effects. This causes environmental pollution. The known sulfur-containing organic compounds and quarternary ammonium compounds cause a problem of generation of unpleasant odor. Some of these compounds also cause a problem of foaming of the water to which they are added.

Japanese Examined Patent Publication (Tokkyo Kokoku) No. Sho-51-33,171 discloses a germicide containing an α-chlorobenzaldoxime acetate derivative of the general formula (I):

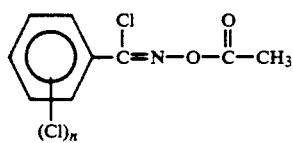

wherein n is an integer of 0 to 2. Japanese Tokkyo Kokoku No. 43-16460 discloses a germicide containing 2-bromo-2-nitro 1,3-diacetyloxypropane of the formula (II):

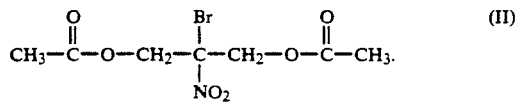

These germicides are effective only against limited kinds of germs and lack durability in germicidal effect.

SUMMARY OF THE INVENTION

The present invention has been made with the foregoing problems of the conventional germicides in view. There is provided in accordance with the present invention a germicidal composition comprising a derivative of α-chlorobenzaldoxime acetate of the formula (I):

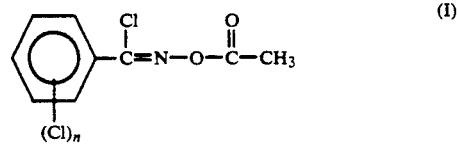

wherein n is an integer of 0 to 2, and 2-bromo-2-nitro-1,3-diacetyloxypropane of the formula (II):

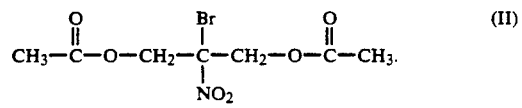

It has been found that when an α-chlorobenzaldoxime acetate derivative of the formula (I) is used in conjunction with 2-bromo-2-nitro-1,3-diacetyloxypropane of the formula (II), a remarkably higher germicidal activity is obtainable than those obtained when they are used singly. Moreover, the germicide containing both of the ingredients of the formulas (I) and (II) exhibits its germicidal effect for a long period of time against a wide variety of germs including filamentous fungi and yeasts.

The present invention will now be described in detail below.

DESCRIPTION OF THE PREFERRED EMBODIMENTS

Examples of the compounds of the formula (I) include α-chlorobenzaldoxime acetate, α-chloro-4-chlorobenzaldoxime acetate and α-chloro-2,4-dichlorobenzaldoxime acetate. These compounds may be used singly or in combination of two or more.

The compounds of the formulas (I) and (II) are used in such a proportion that the weight ratio of the compound (I) to the compound (II) is 1:10 to 10:1, preferably 1:5 to 5:1.

The germicidal composition of the present invention may be suitably in the form of a solution, a dispersion or an emulsion. Thus, a suitable liquid medium, which may be aqueous or organic, may be used for dissolving, dispersing or emulsifying the two germicidal ingredients. An emulsifier such as a surfactant or a stabilizer may be also be used to stabilize the dispersion or emulsion. Examples of organic media include alcohols, ketones, ethers and hydrocarbons. If desired, the germicidal composition may be supported on a solid carrier.

Because of its high synergistic effect, a low concentration of the composition of the present invention can exhibit satisfactory germicidal activities. Thus, for example, when the composition is used for incorporation into industrial water of paper or pulp mills, a concentration of 0.01–100 ppm (calculated as a total weight of the compounds of the formulas (I) and (II)) is sufficient to obtain desired effect. For incorporation into industrial water for use in the field of aqueous coating materials, bonding starch or hides and skins, the concentration is generally 1-500 ppm.

The following examples will further illustrate the present invention. In the examples, "part" and "%" are by weight.

EXAMPLES 1-5

Germicides having the composition shown in Table 1 were prepared.

TABLE 1

|  | Example | | | | |
|---|---|---|---|---|---|
|  | 1 | 2 | 3 | 4 | 5 |
| α-Chlorobenzaldoxime acetate (parts) | 18 | 15 | 10 | 5 | 2 |
| Compound of the Formula (II) (parts) | 2 | 5 | 10 | 15 | 18 |
| Diethylene glycol monomethyl ether (parts) | 77 | 77 | 77 | 77 | 77 |
| RAPISOL B-80* (parts) | 3 | 3 | 3 | 3 | 3 |

*Anionic surfactant, manufactured by Nihon Yushi K.K.

EXAMPLES 6-10

Germicides having the composition shown in Table 2 were prepared.

TABLE 2

|  | Example | | | | |
|---|---|---|---|---|---|
|  | 6 | 7 | 8 | 9 | 10 |
| α-Chloro-4-chlorobenzaldoxime acetate (parts) | 18 | 15 | 10 | 5 | 2 |
| Compound of the Formula (II) (parts) | 2 | 5 | 10 | 15 | 18 |
| Diethylene glycol monomethyl ether (parts) | 77 | 77 | 77 | 77 | 77 |
| RAPISOL B-80 (parts) | 3 | 3 | 3 | 3 | 3 |

COMPARATIVE EXAMPLE 1

A germicide having the following composition was prepared:

| α-Chlorobenzaldoxime acetate | 20 parts |
|---|---|
| Diethylene glycol monomethyl ether | 77 parts |
| RAPISOL B-80 | 3 parts |

COMPARATIVE EXAMPLE 2

A germicide having the following composition was prepared:

| α-Chloro-4-chlorobenzaldoxime acetate | 20 parts |
|---|---|
| Diethylene glycol monomethyl ether | 77 parts |
| RAPISOL B-80 | 3 parts |

COMPARATIVE EXAMPLE 3

A germicide having the following composition was prepared:

| Compound of the Formula (II) | 20 parts |
|---|---|
| Diethylene glycol monomethyl ether | 77 parts |
| RAPISOL B-80 | 3 parts |

The above compositions were subjected to the following tests for evaluating their germicidal properties.

Activity Test

The following germs were used (Indicated in the brackets are abbreviations):

| Pseudomonas aeruginosa | (P.a) |
|---|---|
| Aerobactor aerogenes | (A.a) |
| Bacillus subtilis | (B.s) |
| Alcaligenes viscosus | (A.v) |
| Aspergillus niger | (A.n) |
| Geotrichum sp. | (G.s) |

Each germ was suspended in an aqueous culture medium containing 0.1% peptone, 0.05% glucose, 0.01% potassium hydrogen phosphate and 0.005% magnesium sulfate. A predetermined amount of the suspension was sampled in test tubes to which a predetermined amount (5, 10, 20, 40 and 80 ppm) of the germicidal composition to be tested was mixed. The mixture was cultured with shaking at 32° C. for 24 hours. Thereafter, the degree of growth of the germ was measured by measurement of turbidity. The minimum concentration of the germicidal composition which perfectly prevented the growth of the germ was as shown in Table 3. Each germ was found to grow upon culturing in the absence of the germicide.

TABLE 3

| Example | P.a | A.a | B.s | A.v | A.n | G.s |
|---|---|---|---|---|---|---|
| 1 | <10 | <10 | <10 | <10 | <10 | <10 |
| 2 | <5 | <5 | <5 | <5 | <5 | <5 |
| 3 | <5 | <5 | <5 | <5 | <5 | <10 |
| 4 | <5 | <5 | <5 | <10 | <5 | <5 |
| 5 | <10 | <10 | <5 | <10 | <10 | <10 |
| 6 | <20 | <10 | <10 | <10 | <10 | <10 |
| 7 | <5 | <5 | <5 | <5 | <5 | <5 |
| 8 | <5 | <5 | <5 | <5 | <5 | <5 |
| 9 | <10 | <5 | <5 | <5 | <5 | <5 |
| 10 | <10 | <10 | <10 | <20 | <10 | <10 |
| Comp. 1 | <40 | <40 | <20 | <40 | <40 | <40 |
| Comp. 2 | <40 | <40 | <20 | <40 | <40 | <20 |
| Comp. 3 | <40 | <20 | <20 | <40 | <40 | <40 |

From the results shown in Table 3, it will be appreciated that the germicidal compositions of the present invention can prevent any of the tested germs from growing and the germicidal effect is much better than those obtained when the germicidal ingredients are used by themselves.

Growth Preventing Test (1)

To a recirculating white liquor used in a paper making step of a paper mill was added each of the above germicidal compositions three times per day (2 hours in one time) so that the concentration of the germicide in the white liquor was maintained at 20 ppm. The test was carried out continuously for 7 days. Then the white liquor was sampled to measure the number of germ cells. Thus, the sampled white liquor was diluted with sterilized water and poured into a glass tray in a predetermined amount, to which a Waxman agar culture medium was poured. After gentle mixing, the mixture was allowed to be solidified with a flattened surface and placed in an incubator at 32° C. for 2 days for culturing. Then the colony was counted by a colony counter to give the results shown in Table 4. During the 7 days test, the number of occurrences of paper breakage in the paper making step was counted. The results are also shown in Table 4.

TABLE 4

| Example No. | Number of Cells (per 1 ml) | Number of Occurrence of Paper Breakage |
|---|---|---|
| 1 | $10^2$ or less | 0 |
| 2 | $10^2$ or less | 0 |
| 3 | $10^2$ or less | 0 |
| 4 | $10^2$ or less | 0 |
| 5 | $10^2$ or less | 1 |
| 6 | $10^2$ or less | 0 |
| 7 | $10^2$ or less | 0 |
| 8 | $10^2$ or less | 0 |
| 9 | $10^2$ or less | 0 |
| 10 | $10^2$ or less | 1 |
| Comp. 1 | $4.6 \times 10^4$ | 5 |
| Comp. 2 | $3.8 \times 10^3$ | 6 |
| Comp. 3 | $3.6 \times 10^5$ | 6 |
| Control* | over $10^8$ | 15 |

*no germicide was used.

Growth Preventing Test (2)

To an aqueous paper coating liquid (pH 9.0) of a starch type was added a bouillon liquid medium and a previously rotted, paper coating liquid, to which was added each of the germicidal compositions to a concentration of 300 ppm. The resulting mixture was incubated at 32° C. for 5 days and the number of the living cells was counted. The results are shown in Table 5.

TABLE 5

| Example No. | Number of Cells (per 1 ml) |
|---|---|
| 1 | $8.6 \times 10^3$ |
| 2 | $10^2$ or less |
| 3 | $10^2$ or less |
| 4 | $10^2$ or less |
| 5 | $2.4 \times 10^3$ |
| 6 | $5.9 \times 10^3$ |
| 7 | $10^2$ or less |
| 8 | $10^2$ or less |
| 9 | $10^2$ or less |
| 10 | $4.1 \times 10^3$ |
| Comp. 1 | $1.5 \times 10^7$ |
| Comp. 2 | $2.1 \times 10^5$ |
| Comp. 3 | $1.8 \times 10^5$ |
| Control* | $3.8 \times 10^9$ |

*no germicide was used

What is claimed is:

1. A germicidal composition comprising a synergistic germicidally effective amount of a derivative of α-chlorobenzaldoxime acetate of the formula (I):

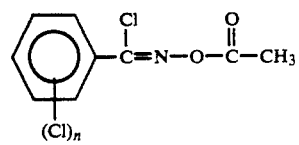

(I)

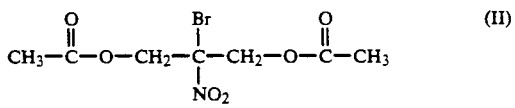

wherein n is an integer of 0 to 2, and 2-bromo-2-nitro-1,3-diacetyloxypropane of the formula (II):

wherein the synergistic weight ratio of the α-chlorobenzaldoxime acetate derivative to the 2-bromo-2-nitro-1,3-diacetyloxypropane is 1:10 to 10:1.

2. A germicidal composition according to claim 1, wherein the synergistic weight ratio of the α-chlorobenzaldoxime acetate derivative to the 2-bromo-2-nitro-1,3-diacetyloxypropane is 1:5 to 5:1.

3. A germicidal composition according to claim 1, further comprising a liquid medium in which the α-chlorobenzaldoxime acetate derivative and the 2-bromo-2-nitro-1,3-diacetyloxypropane are dissolved, dispersed or emulsified.